United States Patent [19]

Feichtinger

[11] 3,967,505

[45] July 6, 1976

[54] METHOD AND MEANS FOR DRAWING SAMPLES FROM MELTS

[75] Inventor: Heinrich Feichtinger, Schaffhausen, Switzerland

[73] Assignee: Leybold-Heraeus-Verwaltung G.m.b.H., Cologne, Germany

[22] Filed: Feb. 27, 1974

[21] Appl. No.: 446,279

[30] Foreign Application Priority Data

Feb. 28, 1973 Switzerland.......................... 2875/73

[52] U.S. Cl.............................. 73/425.6; 73/DIG. 9
[51] Int. Cl.².......................................... G01N 1/14
[58] Field of Search........ 73/DIG. 9, 425.6, 421.5 R

[56] References Cited
UNITED STATES PATENTS

| | | | |
|---|---|---|---|
| 3,315,529 | 4/1967 | Feichtinger | 73/DIG. 9 |
| 3,369,406 | 2/1968 | Lowdermilk et al. | 73/DIG. 9 |
| 3,534,614 | 10/1970 | Creswell | 73/425.6 |

Primary Examiner—James J. Gill
Assistant Examiner—Anthony V. Ciarlante
Attorney, Agent, or Firm—Joseph F. Padlon

[57] ABSTRACT

An arrangement in which samples drawn from a melt are sealed against air, and are allowed to solidify, while the gases given off are collected for analysis. A hollow, thin-walled, metallic element is used, which narrows at its lower end into an orifice. The element is degassed at high temperature before being sealed for use, to remove hydrogen and organic impurities.

11 Claims, 8 Drawing Figures

METHOD AND MEANS FOR DRAWING SAMPLES FROM MELTS

BACKGROUND OF THE INVENTION

The present invention relates to an arrangement, for drawing samples or specimens from melts, in which the drawn samples solidify in the absence of air, and in which the gases emitted during cooling and solidification are quantitatively collected.

In the determination of gas content, as well as certain elements of melts that are subject to change due to the influence of air, the drawing of samples or specimens plays a very large role, for two reasons. First, the melt loses certain gaseous constituents during solidification, particularly $H_2$, CO and in some cases $N_2$, $H_2O$, $CH_4$ as well.

Secondly, in pouring the melt into an open form, the melt reacts with the oxygen and water vapor in air or on the surface of the form. Since the melts, at their extremely high temperatures, have a high affinity and a rapidity of reaction with the gaseous reagents from the air, uncontrollable errors result.

Swiss Pat. No. 409,469 discloses a procedure for drawing samples that permits the determination of the true gas content of melts, whereby the melt flows into a mold after melting through a replaceable meltable cap, which is sealed by rubber rings to the sample form, and flows through a replaceable metal orifice connected to the sample mold by rubber sealing rings. As soon as the mold is filled and the flow of melt ceases, the melt solidifies in the region of the orifice, producing a hermetic seal against the outside atmosphere. Here the mold has to have such thick walls or has to be constructed of a massive amount of copper to conduct away the heat of the incoming melt, to reach a temperature under 70°C. This is required to prevent the elastic seals between orifice and valve from emitting gas or leaking. Any gases that may have been liberated from the sample during solidification, appear between the sample and the wall, as the solidifying melt contracts. These separated gases can be removed through a valve with an elastic seal, and can be fed to an apparatus for analysis.

The gas remaining in the solidified sample can be exactly determined. After removal of the precision-cast, a highly-polished sample from the mold, a portion of the probe can be subjected to heat extraction. The total gas content of the melt is then the sum of the gas emitted during solidification in the mold and the gas found during heat extraction. The amount of hydrogen emitted in this way during solidification is, on the average, 5 – 30% of the total hydrogen content of the melt.

In scientific investigations of thousands of samples with the above procedure, many exact measurements, demonstrating the laws of movement of hydrogen as well as other gases, could be made. However, it became evident that it would be desirable to improve the above procedure fundamentally in several respects for routine application. With the above procedure, all parts must be cleaned very carefully before each application with particularly pure solvents, particularly $CCl_4$, because, e.g., the smallest fractions of a mg. of fat, if it came into contact with the liquid melt, could strongly influence the test results. The parts of the mold have to be combined and highly evacuated before each application, with the sealing being accomplished by elastic seals. This presupposes a certain special know-how, since with improper treatment traces of impurities can strongly influence the precision of the results, as described above.

Accordingly, it is an object of the present invention to provide an arrangement for drawing samples, which retains the advantages of the above procedure, namely: drawing of samples and their solidification under seal against air, and the collection of the gases emitted during and after the solidification. But disadvantages from poor cleaning or from overheating of the sample drawing element or its rubber seals are eliminated.

Another object of the present invention is to provide an arrangement of the foregoing character which is simple in design and may be economically fabricated.

A still further object of the present invention is to provide an arrangement, as described, which is reliable in operation and may be readily maintained.

SUMMARY OF THE INVENTION

The objects of the present invention are achieved by providing an arrangement in which a metallic, thin-walled, hollow element, narrows at its lower end into an orifice. There the element with all its inserts is degassed under protective gas or vacuum at a high temperature (300 – 1200°C.), for particularly removing hydrogen and organic impurities that decompose at high temperatures. It is then evacuated and metalically sealed. Sample from elements that can be constructed from inexpensive, stamped parts, are evacuated at the beginning and sealed metallically, and are capable, in this evacuated state, of practically unlimited storage. They are always ready for use, they do not need to be cleaned before use by the person applying them, but are brought to a standard of cleanliness not possible with known procedures. This is accomplished by glow and degassing under vacuum, producing, in particular, freedom from hydrogen.

While the known procedure was so constituted that the mold could be used over and over with cleaning and replacement of a new cap and a new orifice, the new element for drawing samples is intended for a single application. Therefore it becomes far lass expensive and more favorable with respect to weight than the relatively expensive and heavy copper molds in the old procedure.

The advantage of these new elements for drawing samples lies above all in their readiness for rapid use and their analytical reliability. With few operations they can be inserted into a submersion facility. The drawing of samples by submersion in the melt requires very little time, since the actual submersion time, as well as the filling of the sample form element with melt, requires only 0.2 – 1 sec. After the cooling time, the element for drawing samples is drilled under seal against air, so that the emitted gases, particularly hydrogen, can be lead off to conventional analytical apparatus. The remaining elements to be determined in the solidified sample, are obtained through cutting open the element for drawing samples with, e.g., a cutting disc, removing the solidified sample, and subjecting it to further analytical procedures.

A further advantage of the procedure according to the invention is that the element for drawing samples, even when it is subjected to high temperatures, never leaks. Nor does it render the analytic results useless through the development of secondary gases, as is unavoidably the case with the use of elastic seals in the known procedures. Thus it is also possible to extract the hydrogen in its entirety from certain materials. This is possible because means are provided for maintaining the sample in the element for drawing samples at a high temperature, thus extracting the hydrogen shortly after drawing from the solidified sample in the element for drawing samples.

Thus, according to the invention there is obtained a procedure which permits a precise and rapid determination of the hydrogen content of melts, since shortly after drawing, the largest portion of the hydrogen has diffused from the drawn sample and is present in the collection spaces of the element for drawing samples, from which it can be removed after drilling and analytically determined.

A further advantage of the procedure, according to the invention, consists of the feature that with melts which emit water vapor during the drawing process, (which is of particular importance for the analysis of pure copper melts, for example) the water vapor reacts with reagents brought into the collection space to form hydrogen, acetylene, and other gaseous substances that are analytically and easily determinable.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figures 1, 2:
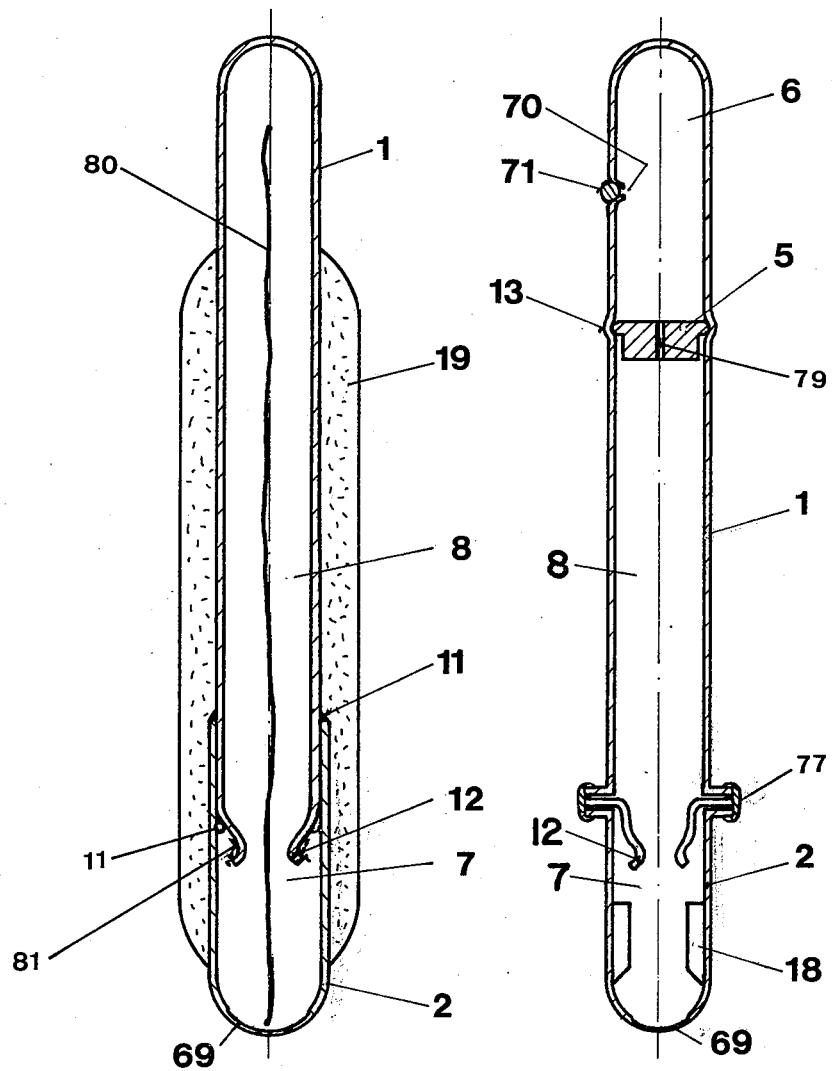
FIG. 1 is an elevational view and shows a simply-constructed embodiment of an element for drawing samples, in accordance with the present invention.
FIG. 2 shows a second embodiment of an element for drawing samples.

Referring to the drawing, FIG. 1 shows an element for drawing samples consisting of a housing 1 ending in a narrow aperture 12. After degassing through glow in a protective gas or in vacuum, the meltable cap 2 is metallically attached and sealed to housing 1 at point 11. The meltable cap can have, at point 69, a smaller thickness of wall (0.1 – 1 mm). Later, when the element is submerged in the melt, this wall melts easily, which also minimizes the amount of material from the meltable cap entering the sample that is to be drawn into the space 8. The entire element for drawing samples can be covered on a part of its surface, especially where an attack by the melt on submersion into the melt is to be avoided, by a protective coating 19, e.g., a finish. This protective coating 19 is applied after closing the element for drawing samples 1, 2.

The meltable cap 2 must in each case be constructed of such a metal that, on drawing the sample from the melt, no disturbing additives can enter the drawn sample. The aperture 12, on the other hand, must consist of such a metal that it forms a good metallic seal with the inflowing melt.

With steel melts it has been found advantageous to use meltable cap 2 as well as orifices 12 made of steel, since this material has the same melting point as the melt, and closes well at 12 with partial heat-sealing. With copper melts, copper is advantageous as the material for the meltable cap 2 and the orifice 12. With aluminum or aluminum alloy melts it is favorable to construct the meltable cap 2 from aluminum. The orifice, however, should be of steel, copper, or aluminum. If steel or copper are used for the orifice 12, it is necessary, particularly with those metals that do not weld with a good seal with other metals, to apply to the orifice 12, tin, copper, silver, silver solder, or similar materials that form a well-sealing metallic connection with the drawn melt sample after solidification. Since these connecting materials are entirely degassed, according to the invention, before the final closure of the element for drawing samples, there is no uncontrolled gas absorption by the drawn melt sample.

With highly-agitated melts of e.g., steel, an aluminum wire 80 can be inserted into the space 7 and 8, which is well degassed during the degassing procedure prior to closure of the element for drawing samples, and is continually sealed from air until the sample is drawn. After the sample is drawn, the insert 80 at least partially binds the oxygen content of the drawn sample, without drawing any hydrogen into the sample.

It has been found in practice that a sample entering the element for drawing samples usually does not form a heat seal with the walls of the housing 1, except at orifice 12. If such a heat seal is to be avoided with increased certainty, it is possible to provide the inner wall of housing 1 with a thin isolating coating, as for example by coating with a finish (not shown in the drawing). Here care must be taken to insure that the orifice 12 is absolutely free of such a coating finish. It is understood that the glow degassing process is of considerably greater duration with a housing 1 that has been provided with an isolating coating on its inside. The drawing of the sample occurs through submersion of the meltable cap 2 in the melt. This occurs preferably with the aid of a submersion facility as described below. After the meltable cap 2 has melted through, particularly in the area 69, the melt spurts through space 7 and orifice 12 into the space 8 of the element for drawing samples, and fills the element in substantially a fraction of a second. As soon as the melt stops flowing, the solidification process begins, and this seals the orifice 12 hermetically against the outside atmosphere.

In those cases, in which, e.g., solder has been applied at 81, a well-sealing connection is established even between metals where a good weld is often obtained only with difficulty, e.g., when orifice 12 consists of copper or steel but has a tin or silver coating, and the drawn sample consists of an aluminum alloy. As soon as the melt has solidified, it contracts, and there is a liberation of gases between the housing 1 and the melt sample solidified in space 8.

For analytical determination, according to the procedure described below, the gases separated during the solidification are removed. This is done by drilling into the element for drawing samples under seal against air, and connecting the element to apparatus for analyzing the gases. Finally, the sample solidified in space 8 is removed from the space, by cutting open the housing 1, for example, in the area above the orifice 12 with a cutting disc. The extracted sample is cut up and analyzed further by such processes as heat extraction, spectral analysis, C-determination, etc.

FIG. 2 shows an element for drawing samples in which a closing element 5, divides the inner space of the element into part 8 and part 6. The closing element 5 can be held in position by a flange 13 or by other means. The closing element 5 accomplishes prevention of the entry of melt sample from space 8 into space 6, but must allow liberated gases to pass from space 8 into space 6. If the closing element 5 is constructed of metal or of ceramic material allowing no gas to penetrate, it has been found advantageous to provide element 5 with one or more holes 79 of such small diameter (0.1 to 1 mm) that the melt solidifies when it enters them. It has also been found advantageous to construct such closing elements 5 from porous, heat-resistant, ceramic material (e.g., $SiO_2$, $Al_2O_3$) or graphite, the pores of which allow easy passage of gas while holding back the melt.

The insertion of a guiding member 18 for the melt, for example, of $SiO_2$, $Al_2O_3$, or glass, causes the melt to flow centrally into the orifice 12, favoring a faster solidification of the melt in the outer area of orifice 12. FIG. 2 also shows the final closure 77 of the element for drawing samples, accomplished simultaneously with the evacuation of the element. This must be metallic, sealing connection, which must be accomplished under vacuum, and can consist, e.g., of butt welding, electric welding, soldering, etc. It is also possible to accomplish closure at this point by a metallic deformation carried out under vacuum. It is also possible to degas and evacuate the element for drawing samples at a high temperature after it has had the metallic sealing meltable cap 2 attached. This is done by drilling a hole 70, which must be finally closed by soldering or welding 71 under vacuum.

Figure 3:
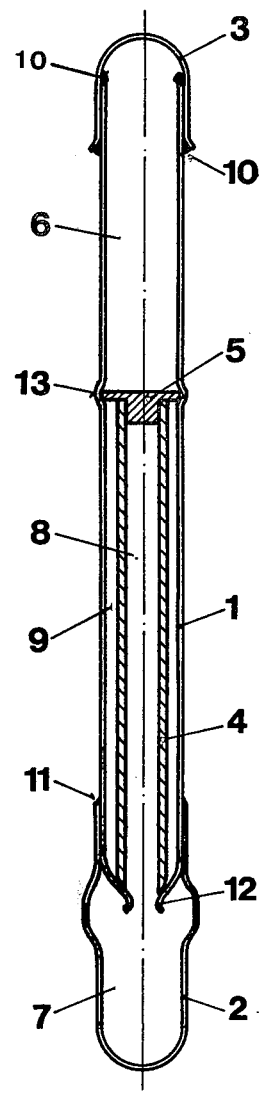
FIG. 3 shows an element for drawing samples with inserted parts that cause the sample to solidify while separated from the walls of the element.

FIG. 3 shows an element for drawing samples, in which the melt enters an inserted pipe 4, which is held and centered by the closing element 5, that allows the passage of gas. The inserted pipe 4 can be made of ceramic material, e.g., $SiO_2$, $Al_2O_3$ or metal; or of porous material: graphite, ceramic sintered materials, etc. If porous, gas-passing material is used for the inserted pipe 4, this part can be made in one piece with closing element 5. In FIG. 3, closure of the element for drawing samples is accomplished, after glow and degassing, by a cap 3, which is closed, for example, at point 10 by soldering under vacuum.

Figure 4:
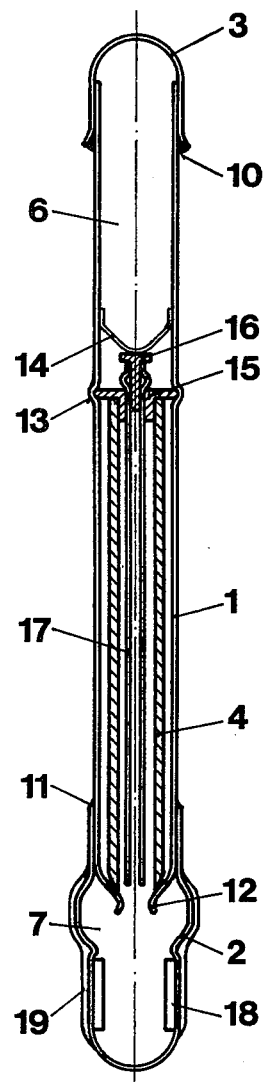
FIG. 4 shows an element for drawing samples containing inserted parts causing an increase in the solidifying surface of the melt, and causing faster gas emission from the melt.

FIG. 4 shows an element for drawing samples, which contains a second insertion pipe 17 within inserted pipe 4, providing a much enlarged surface to the inflowing metal, causing it to solidify as a thin layer. This accomplishes that the gases emitted from the melt, particularly hydrogen, can leave the solidifying melt more rapidly. As a rule, heatresistant materials, e.g., $SiO_3$, $Al_2O_3$, and similar materials are used for the inserted pipe 17. In FIG. 4, the centering closing element is designated by 15 and the closing element for inserted pipe 17 is designated by 16. Element 14 is a spring for keeping closing element 16 in position and for support of inserted pipes 4 and 17.

Figures 5, 6:
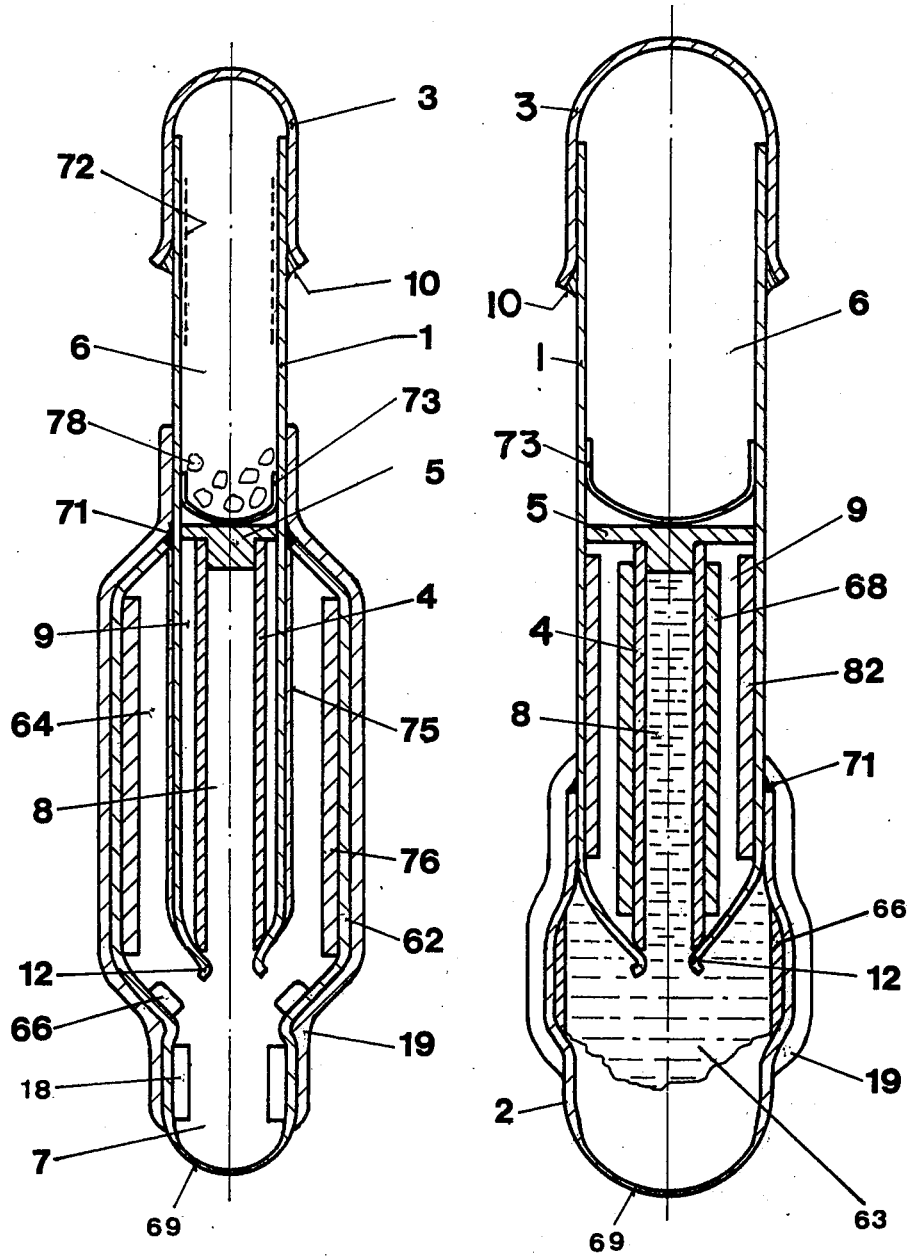
FIG. 5 shows an element for drawing samples, in which an additional volume of melt is drawn separately and simultaneously with the sample, causing the sample to remain at a higher temperature for a longer time.
FIG. 6 shows an element for drawing samples constructed as a heat storage element, so that the heat contained in the melt is retained for a longer time.

FIG. 5 shows an element for drawing samples, in which the lower meltable cap 62 is widened and lengthened, and metallically connected to housing 1 at point 71. Thus, there arises a space 64, which has approximately the length of the inserted pipe 4. As soon as the element for drawing samples is submerged in the melt, the melt enters at point 69 into space 7, and from there it fills space 64 and space 8 simultaneously. The solidification produces a sealing closure at 12. By means of cooling insertions 66, the solidification in the vicinity of orifice 12 can be accelerated. A coating finish 75 protects the housing 1 from direct attack of the melt. A heat-isolating insertion 76 protects the walls of meltable closing cap 62. Moreover, in the embodiment of FIG. 5, coating 19 prevents an attack by the melt on the meltable cap from the outside.

It is possible to introduce reagents, e.g., Li, Ca, Mg, Al, $CaC_2$, and others into the element for drawing samples at points 72 or 78, which react with water vapor to produce hydrogen or acetylene. This is of importance when melts giving off water vapor on solidification are drawn. The purpose of the construction shown in FIG. 5 is that the solidifying sample in space 8 is kept for a longer time at an elevated temperature (400° – 950°C.), by the additional melt solidifying in space 64. This accomplishes that the sample in space 8 emits a particularly large portion of diffusable, gaseous products, which are collected in spaces 9 and 6. With this procedure, it is often advantageous to construct the inserted pipe 4 as well as the closing element 5 from porous material, e.g., pure graphite.

FIG. 6 shows another embodiment for the prolonged heat retention of the sample contained in space 8. In this case, the inserted pipe 4 is surrounded by a heat-storing radiation shield 68. Insert 82 is of heat-insulating material. Near 63 it is shown how the solidifying melt closes the orifice 12 after the drawing is completed. The sample mass glowing and solidifying in space 8 yields its heat by conduction and/or radiation to the inserted pipe 4 and the heat-storing radiation shield 68.

It has been found advantageous to choose the relationship of the weight of heat storage element 68 to the weight of the drawn sample in 8 in such a way that the inflowing metal and the heat storage element 68 reach a temperature of 600° – 900°C. With steel, having a melting point of 1600°C., theoretically the heat storage capacity of the parts 4 and 68 should be one third of the capacity of the steel melt solidifying in space 8, resulting in a temperature of about 1060°C. In practice, however, measurements have shown a resulting temperature of 850° – 900°C. According to the law of heat radiation, it is easily understandable that the cooling time of the melt solidifying in space 8 is stretched to several minutes by correct dimensioning of the insert 68. This is sufficient to allow the largest portion of the hydrogen from the solidified sample in space 8 to escape, especially if the space 6 is sufficiently large. For most analytical purposes it is sufficient to make the space 6 from 5 to 50 cubic centimeters. The smaller the weight of the sample in space 8, which can be, e.g., 1 to 20 g., the smaller can be the space 6. The optimum results depend on melting point and heat storage capacity of a melt, including the heat of fusion, from which the most favorable relationship of the weight of drawn melt to the weight of insert 68 can be easily calculated.

Figure 7:
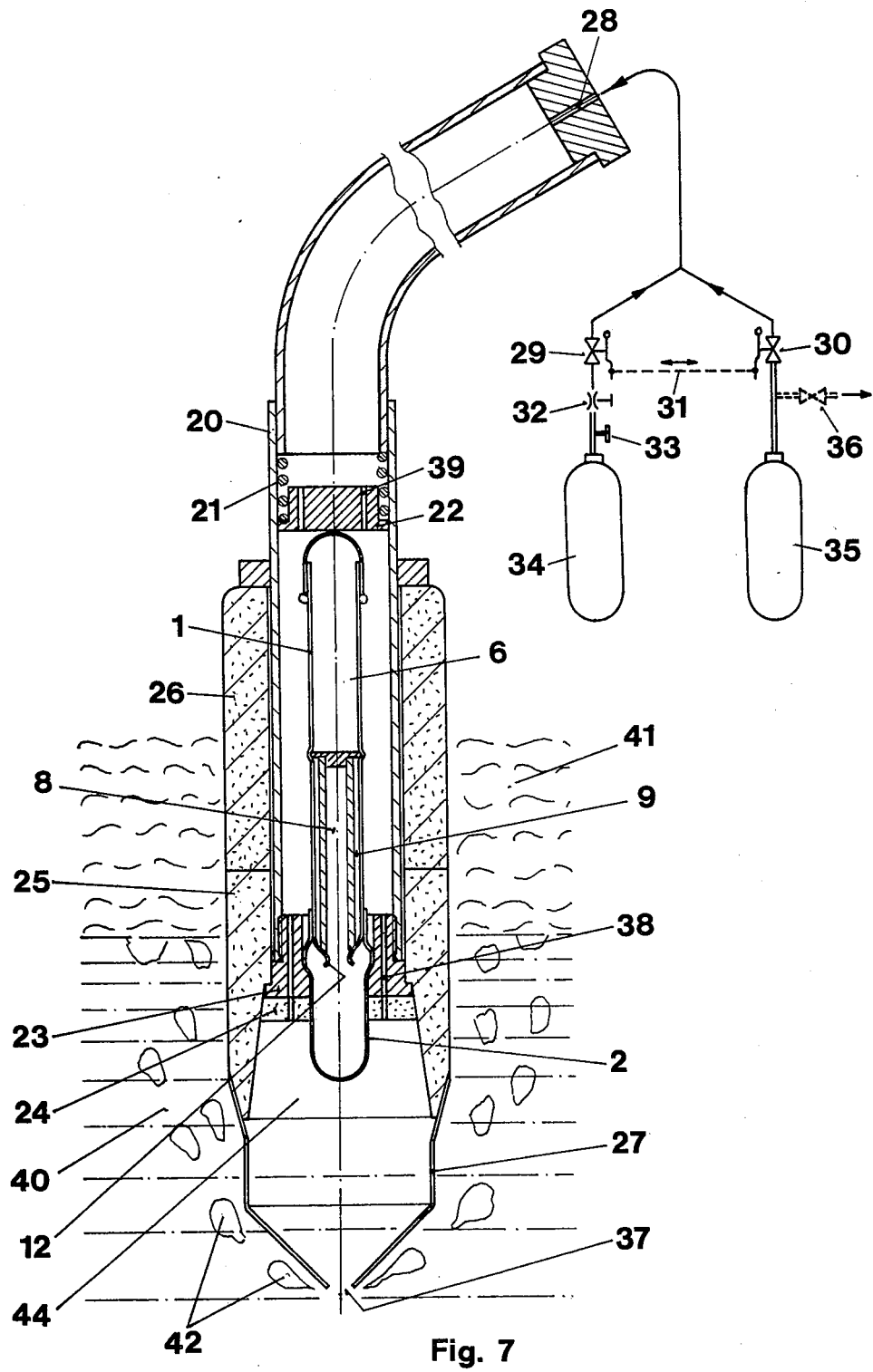
FIG. 7 shows schematically a submersion facility with an inserted element for drawing samples according to the invention.

FIG. 7 shows a submersion facility with inserted element for drawing samples, where the element is held in place by inserts 22 and 23 within the submersion pipe 20. A spring 21 holds, for example, insert 22. Insert 23 is protected by insulation 24 from attack of the melt. The submersion pipe 20 is, furthermore, protected by protective heat-insulating housings 25, 26, and 27 against melt, slag, etc., to the depth of submersion. During submersion it is possible to feed protective gas, e.g., argon, into the submersion facility, namely from the protective gas reserve vessel 34 through open valves 33 and 29, preventing thereby entry of the space 44. By means of cap 27, having at its bottom, or perhaps on the side, an opening 37, the ability to submerge through layers of slag 41 can be improved. Here the entry of slag into the space 44 is prevented by continued blowing of protective gas from the reserve vessel 34.

The protective cap 27, too, can be protected against too rapid an attack of melt and slag by a protective coating, e.g., a finish which is not shown. As soon as the submersion facility enters the melt 40, the cap 27 melts off in a direction from the bottom upwards. During this entire time, protective gas is allowed to flow from the reserve vessel 34 through the submersion facility 20, so that a pressure is maintained in space 44, with bubbles 42 escaping.

The use of protective gas is of particular importance because the parts of the melting cap 27 are removed by the bubbles from the actual sample. The optimum gas flow can be adjusted, e.g., by a needle valve or a throttle. The actual drawing of the sample occurs, after the prescribed depth has been reached, in that simultaneously valve 29 is closed while valve 30 is opened, as indicated by connection 31. With valve 36 open, the melt would rise in space 44 due to the hydrostatic pressure in space 44 after the disappearance of the excess pressure in the submersion facility. Meanwhile, the gases present in space 44 can leave through the path 38, 39, 28, 30, 36.

In many cases, in which an accelerated rise of the melt in space is desired, a source of vacuum 35 can speed up the departure of the gases from space 44 with valve 36 closed and valve 30 open. After resetting the valves 29 and 30 the melt spurts into space 44, hits protective insulator 24, and is held up at insert 23 having thin passages at 38. These passages have such small diameters that the melt solidifies immediately on entering them. The solidification is particularly rapid when the insert 23 is made of a good heat-conducting material, preferably a material with a lower melting point than that of the melt. The melt rising in space 44 melts through cap 2, spurts into the space 8, and closes the orifice 12 through solidification and heat sealing. The entire submersion procedure can be rapidly carried out. The melting of cap 2 and the filling of space 8 generally takes only fractions of a second. The person operating the submersion facility merely has to operate valves 29, 30, everything else proceeds independently of subjective influences.

The submersion facility must now be removed from the melt. The element for drawing samples 1, now filled with the sample, is removed from the submersion facility. The sample is now solidified in space 8, and is hermetically sealed against the influence of the atmosphere by the welded orifice 12. The gases emitted by the sample can only enter the spaces 6 and 9, and remain there until the analytic determination.

Figure 8:
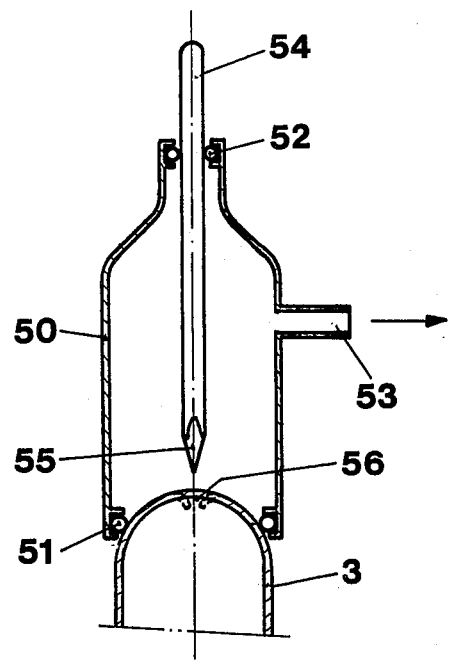
FIG. 8 shows a facility for drilling into the element for drawing samples in a hermetically-sealed manner by means of which emitted gases can be led off for analytical determinations.

FIG. 8 shows a gas removal hood 50, which permits total removal of the gases emitted by the melt during solidification in the element for drawing samples. The function of the hood 50 is as follows: With the aid of the rubber seal 51 the hood is set in an airtight manner on the element for drawing samples, e.g., on the cap 3. Now the inside of the hood 50 is evacuated, then a hole 56 is made by a drill or puncturing device 54 into the wall of the element for drawing samples. In FIG. 8 this is illustrated by a hammered device, in which the stylus 54 is driven through the rubber seal 52 so that its point 55 penetrates the cap 3. Instead of the puncturing device 54, a spiral drill could also be used. Point 53 is the connection for feeding the gases pumped from opening 56 to conventional apparatus for the analysis of gases.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

I claim:

1. An arrangement for drawing a sample from melts comprising, in combination, a tube-shaped evacuated hollow element capable of being heated to a temperature sufficient to degass said element during evacuation, the drawn sample solidifying in said element in the absence of air; the gases emitted by said sample during solidification and cooling being collected quantitatively within said element; an orifice-shaped narrowed portion within the interior of said hollow element and in vacuum-tight communication with said drawn sample, said hollow element having a thin-walled metallic sleeve-shaped member and a covering cap; and metallic sealing means for sealing the exterior wall of said element vacuum tight; insert means within said element for subdividing the interior of said element into an upper chamber and a lower chamber, said insert means passing gases into said upper chamber and inhibiting the passage of melt through said insert means.

2. The arrangement as defined in claim 1 including insert tube means within said element and concentric to the wall of said element, said insert tube means being between said orifice-shaped narrowed portion and said insert means.

3. The arrangement as defined in claim 2 wherein said insert tube means is comprised of ceramic material.

4. The arrangement as defined in claim 2 wherein said insert tube means is comprised of porous material.

5. The arrangement as defined in claim 2 wherein said insert tube means is comprised of reactive materials for reacting with the drawn sample to form gaseous compounds.

6. The arrangement as defined in claim 2 including heat storage means within the space between said element and said insert tube means and attaining a temperature of 400°C. to 950°C. depending on the thermal capacity of said heat storage means and the heat content of said sample shortly after being drawn.

7. The arrangement as defined in claim 6 wherein said member is comprised of a reactive material convertible to a permanent gas with water vapor.

8. The arrangement as defined in claim 1 including means in said upper chamber for accummulating reactive ingredients convertible to permanent gases with water vapor.

9. The arrangement as defined in claim 1 including an auxiliary tube within said insert means.

10. The arrangement as defined in claim 1 wherein said sealing means is broadened and surrounds said element for a length corresponding substantially to the length of said insert means, said sealing means being connected metallically tight to said element at the location of said insert means.

11. The arrangement as defined in claim 1, including; insert tube means within said element and concentric to the wall of said element, said insert tube means being between said orifice-shaped narrowed portion and said insert means, said insert tube means being comprised of porous material, said upper chamber accummulating reactive ingredients convertible to permanent gases with water vapor, said sealing means being broadened and surrounding said element for a length corresponding substantially to the length of said insert means, said sealing means being connected metallically-tight to said element at the location of said insert means; a member within the space between said element and said insert tube means and attaining a temperature of 400°C. to 950°C., depending on the thermal capacity of said member and the heat content of said sample shortly after being drawn, said member being comprised of reactive material convertible to a permanent gas with water vapor; cap means at the end of said element facing said orifice-shaped narrowed portion for forming a vacuum-tight closure, said element being comprised of a plurality of parts, said cap means being of metal.

* * * * *